United States Patent [19]

Arter et al.

[11] Patent Number: 5,185,249
[45] Date of Patent: Feb. 9, 1993

[54] DRY ANALYTICAL ELEMENT FOR ASSAYING SALICYLATE

[75] Inventors: Thomas C. Arter; Bonny A. Harris, both of Rochester; James R. Schaeffer, Penfield, all of N.Y.

[73] Assignee: Eastman Kodak Company, Rochester, N.Y.

[21] Appl. No.: 504,204

[22] Filed: Apr. 4, 1990

[51] Int. Cl.⁵ .................. C12Q 1/26; C12Q 1/32; C12Q 1/28
[52] U.S. Cl. ........................ 435/25; 435/26; 435/28
[58] Field of Search ............... 435/25, 26, 28

[56] References Cited

U.S. PATENT DOCUMENTS

| | | | |
|---|---|---|---|
| 3,992,158 | 11/1976 | Pryzbylowicz | 422/58 |
| 4,416,983 | 11/1983 | Röder et al. | 435/25 |
| 4,439,278 | 6/1989 | Terashima et al. | 435/21 |
| 4,919,890 | 4/1990 | Arai et al. | 435/28 |

Primary Examiner—Douglas W. Robinson
Assistant Examiner—Jon P. Weber
Attorney, Agent, or Firm—John R. Everett

[57] ABSTRACT

A dry multilayer element for assaying salicylate is disclosed.

8 Claims, No Drawings

DRY ANALYTICAL ELEMENT FOR ASSAYING SALICYLATE

FIELD OF THE INVENTION

This invention relates to clinical chemistry. It provides an analytical element for the assay of salicylate.

BACKGROUND OF THE INVENTION

The determination of salicylate in biological fluids such as human serum, has diagnostic significance. Acetylsalicylic acid (aspirin) is used as an analgesic and as an anti-inflammatory drug for arthritis. It rapidly hydrolyzes to salicylate which has the therapeutic affect and a long half life. The therapeutic level as an analgesic is up to 20 mg/dl. For arthritis the level is up to 30 mg/dl. Problems such as headaches, tinnitus, flushing and hyperventilation occur at higher salicylate levels followed by imbalances in the acid-base level. Salicylate levels above 60 mg/dl can be lethal.

U.S. Pat. No. 4,416,983 discloses a solution method for the determination of salicylate in body serums. The method is based on the following chemical reaction:

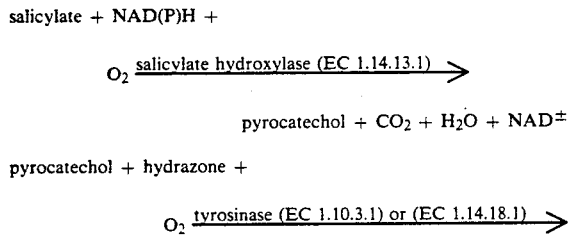

salicylate + NAD(P)H + $O_2$ $\xrightarrow{\text{salicylate hydroxylase (EC 1.14.13.1)}}$ pyrocatechol + $CO_2$ + $H_2O$ + $NAD^\pm$ pyrocatechol + hydrazone + $O_2$ $\xrightarrow{\text{tyrosinase (EC 1.10.3.1) or (EC 1.14.18.1)}}$ The method as carried out in U.S. Pat. No. 4,416,983 is a wet assay in which the two chemical reactions listed above are carried out simultaneously in one vessel. That is, all the chemical reagents needed to conduct the reactions are included in a single solution to which the salicylate contained in the sample is added.

That method as disclosed is not adaptable for dry analytical elements. The problem is that elements in which all of the reagents are included in a single layer as taught by U.S. Pat. No. 4,416,983, have poor storage life. Work in our labs has shown that the life of the element as measured by its ability to respond to salicylate in a sample, is very short. The salicylate hydroxylase activity drops upon continued exposure to the hydrazone coupling agent. This problem on the solution thereto is not taught in any of the prior art of which the inventors are aware.

SUMMARY OF THE INVENTION

The present invention provides a multilayer analytical element comprising a support coated in the following order, top down to the support:
a) a spreading layer,
b) a dye layer comprising tyrosinase and a hydrazone coupling agent,
c) a reagent layer comprising salicylate hydroxylase and nicotinamide adenine dinucleotide (NADH), characterized in that
d) the dye layer has a pH greater than 6.5;
e) the dye layer and reagent layer are separated by a barrier layer that prevents passage of molecules having a molecular weight in excess of 5,000, and
f) the hydrazone coupling agent is water insoluble at a pH above 6.5.

The present invention represents an unexpected improvement over the prior art. The colored hydrazone catechol complex is easily measured because of its high extinction coefficient. The complex is sufficiently formed within 5 minutes to allow effective measurement of the salicylate concentration colorimetrically. Due to the physical separation of the salicylate hydroxylase from the hydrazone coupling agent, the element stability during storage is greatly lengthened and response is increased. The use of a $TiO_2$ pigmented spreading layer also reduces many spectral and turbidity driven interferences seen in wet element systems.

In this element, the two reactions described above upon which the assay is based are carried out sequentially in separate layers of the element. The barrier layer does not allow passage of molecules having a molecular weight larger than 5,000. Salicylate hydroxylase has a reported molecular weight of 91,000. Thus it is trapped in the bottom layer below the barrier layer. The hydrazone coupling agent as a hydrochloride is water soluble, but at pH above 6.5, the hydrochloride is removed and the dye precipitates out of solution. In the analytical element of this invention, the hydrazone coupling agent is coated in an unbuffered gelatin layer at pH 5.5 over a pH 8 buffered barrier layer. Once coated and dried, the top barrier layer is also at a pH of 8, from buffer that has diffused up from the lower gelatin layer. As the pH increases, the 3-methyl-2-benzothiazolinone hydrazone hydrochlorine (MBTH) drops out of solution and become crystalline in nature. In this form MBTH of the hydrazone coupling agent cannot diffuse down through the intervening barrier layer that separates it from salicylate hydroxylase. Thus, the hydrazone coupling agent differs from that disclosed in U.S. Pat. No. 4,416,983 in that the hydrazone coupling agent disclosed in that is water-soluble at a pH above 6.5.

The present invention also discloses a method for assaying biological fluids for salicylate comprising the steps of:
a) spotting the slide analytical element described above with a sample suspected of containing salicylate;
b) allowing an incubation time of at least about 3 to 5 minutes; and
c) making a colorimetric determination of the colorimetric qualitative assay of the salicylate present in the sample.

DETAILED DESCRIPTION OF THE INVENTION

The element of this invention can be used to assay salicylate qualitatively and quantitatively in biological fluids in animals or humans, but preferably of humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

Elements of the invention can be configured in a variety of forms, including elongated tapes of any desired width, sheets, slides or chips.

The elements can be used in manual or automated assay techniques. In general, in using the elements, salicylate determination is made by taking the element from a supply roll, chip packet or other source and physically contacting it with a sample (for example, up to 200 μl) of the liquid to be tested so that the sample and reagents interact sequentially within the element become mixed. Such contact can be accomplished in any suitable manner, for example, by dipping or immersing the element into the sample or, preferably, by spotting the element by hand or machine with a drop of the sample with a suitable dispensing means.

After sample application, the element is incubated, for a period of up to 5 minutes, to facilitate color development. By incubation, we simply mean that the reagents are maintained in contact with each other for a period of up to 5 minutes before color measurements are made.

The dry analytical elements of this invention are multilayered. At least one of the layers is preferably a porous spreading zone. The other layers include a reagent layer and a dye layer. The reagent layer includes a barrier zone and a reagent zone. All of the foregoing layers are coated on a support. The layers are generally in fluid contact with each other, meaning that fluids, reagents and reaction products (for example, color dyes) can pass or be transported between superposed regions of adjacent zones. In other words, when the element is contacted with an aqueous fluid, all reagents of the analytical composition of this invention mixed sequentially as stated hereinbefore and can readily move within the element as a composition. Each layer can be separate or two or more zones can be separate areas in a single layer of the element. Besides the references noted above, suitable element components are described also, for example, in U.S. Pat. Nos. 4,042,335 (issued Aug. 16, 1977 to Clément), 4,132,528 (issued Jan. 2, 1979 to Eikenberry et al.), and 4,144,306 (issued Mar. 13, 1979 to Figueras).

Useful spreading layers can be prepared using fibrous materials, either mixed with a suitable binder material or woven into a fabric, as described in U.S. Pat. No. 4,292,272 (issued Sep. 29, 1981 to Kitajima et al.), polymeric compositions or particulate materials, for example a blush polymer such as disclosed in U.S. Pat. No. 3,992,158, beads bound together with or without binding adhesives, as described in U.S. Pat. Nos. 4,258,001 (issued Mar. 24, 1981 to Pierce et al.) and 4,430,436 (issued Feb. 7, 1984 to Koyama et al.) and Japanese Patent Publication 57(1982)-101760. Particularly useful spreading layers comprise barium sulphate or titanium dioxide. Since the sample is generally applied directly to the spreading layer, it is desirable that the spreading layer be isotropically porous, meaning that the porosity is the same in each direction in the layer as caused by interconnected spaces or pores between particles, fibers or polymeric strands.

The layers can be coated on transparent supports such as polyethylene terephthalate. Other supports are well known in the art.

The elements of this invention can also contain one or more other addenda commonly put in the elements for various manufacturing or operational advantages. Such addenda include surfactants, buffers, solvents, hardeners and other materials known in the art.

The following examples clearly establish the improved aspects of the present invention.

COMPARATIVE EXAMPLE

A Reagent Element in Which All of the Reagents are Included in the Single Layer as Taught by U.S. Pat. No. 4,416,983

When all the reaction chemicals are containing in a single element layer the life of the element, as measured by its ability to respond to salicylate, was very short. The salicylate hydroxylase activity dropped upon continuous exposure to the hydrazone (MBTH). Although the reaction ingredients could function together in a wet system, separation was required to achieve a practical element life in a dry system.

| Combined System Element: | | $g/m^2$ |
|---|---|---|
| Spreading Layer | $BaSO_4$ pigment | 107.6 |
| | Estane 5715 binder | 1.08 |
| | Cellulose acetate binder | 8.6 |
| | I-100 (poly-N-isopropyl-acrylamide) binder | .4 |
| | TX-405 surfactant | 2.1 |
| Reagent Layer | DI type IV gelatin binder | 12.0 |
| | Potassium phosphate buffer | 3.0 |
| | Sodium chloride | 1.5 |
| | Bis(vinylsulfonylmethyl) ether hardener | .24 |
| | 3-Methyl-2-benzothiazolinone hydrazone hydrochlorine (MBTH) | .25 |
| | Tyrosinase | 100,000 units/$m^2$ |
| | Nicotinamide adenine dinucleotide (NADH) | .76 |
| | Salicylate hydroxylase pH 7.6 | 1,000 units/$m^2$ |
| Support | Poly(ethylene terephthalate) | |

Estane 5715 binder is a commercially available polyurethane binder.

When spotted with serum containing 100 mg/dL of salicylate the following reflection density response was measured over time at 540 nm.

| Initial Time | Two Days at 25° C. | Five Days at 25° C. |
|---|---|---|
| .64 | .37 | .21 |

Addition of more salicylate hydroxylase to the element would allow it to temporarily regain its initial response to salicylate. Solution studies showed that it was the presence of MBTH that caused the loss of salicylate hydroxylase activity:

| | Time Zero | 30 Minutes at 4° C. |
|---|---|---|
| Salicylate Hydroxylase | 33.4 u/L | 36.2 u/L |
| Salicylate Hydroxylase with 3-Methyl-2-benzothiazolinone hydrazone hydrochlorine (MBTH) | 33.4 u/L | 28.2 u/L |

Separation of the salicylate hydroxylase and the hydrazone was required to achieve adequate element storage life.

EXAMPLE 1

The Present Invention

| Element Structure and Content: | g/m² | Range g/m² |
|---|---|---|
| Spreading Layer | | |
| TiO₂ pigment | 50.0 | 20–100 |
| Estane 5715 | 2.5 | .2–10 |
| Cellulose acetate binder | 6.9 | 2–20 |
| Poly-N-isopropylacrylamide binder | .4 | .05–2 |
| TX-405 surfactant | 1.6 | 0–4 |
| Oleyl PEG surfactant | .8 | 0–3 |
| Dye Layer | | |
| DI type IV gelatin binder | 6.0 | .2–15 |
| Sodium chloride | .5 | 0–4 |
| Bis(vinylsulfonylmethyl)-ether hardener | .1 | .01–1 |
| 3-Methyl-2-benzothiazolinone hydrazone | .4 | .05–2 |
| Tyrosinase | 80,000 U/m² | 5–300K |
| pH | 5.2 | 3–6.5 |
| Reagent Layer | | |
| Barrier Zone | | |
| DI type IV gelatin binder | 6.0 | .2–15 |
| Bicine buffer | 1.5 | .2–5 |
| Sodium chloride | .5 | 0–4 |
| Bis(vinylsulfonylmethyl)ether | .1 | .02–1 |
| Nicotinamide adenine dinucleotide | 1.0 | .1–4 |
| pH | 7.8 | 6.5–9.0 |
| Reagent Zone | | |
| DI type IV gelatin binder | 6.0 | .2–15 |
| Bicine buffer | 1.5 | .2–5 |
| Sodium chloride | .5 | 0–4 |
| Bis(vinylsulfonylmethyl)ether | .1 | .02–1 |
| Salicylate hydroxylase | 576 U/m² | 100–5K |
| pH | 7.8 | 6.5–9.0 |
| Support | | |
| Poly(ethylene terephthalate) | | |

When spotted with serum containing 100 mg/dL of salicylate the following density response was measured over time at 540 nm.

| Initial Time | 7 Days at 25° C. | 14 Days at 25° C. | 28 Days at 25° C. |
|---|---|---|---|
| 1.27 | 1.27 | 1.27 | 1.25 |

The element was stable over time. The absolute response was greater than even the initial response in the case where the hydrazone and the salicylate hydrolase are in the same layer. The tyrosinase was moved into the same layer or zone with MBTH as neither could move in the element and they need to be in contact to function optimally. Separation is achieved even after rewetting with the sample as hardened gelatin will not allow passage of proteins or enzymes of greater than 5,000 molecular weight and the MBTH is not water soluble at a pH greater than 6.5. The combination of these two affects prevents the MBTH and the salicylate hydroxylase from coming into contact during manufacture or storage. Contact upon rewetting is not necessary as long as the catechol can readily diffuse between layers.

The MBTH is coated in a solution at pH 5.5 at which it is water soluble. Once it has been coated over the underlying gelatin layers containing buffer at pH 7.8 and the pH of the MBTH layer also increases to 7.8 and the MBTH becomes insoluble in water and thus immobile.

The usefulness of this element as a method of quantifying salicylate concentration in serum or other fluids is shown in the following table:

| Reference Salicylate mg/dL | No. of Tests | Dr | Predicted Values | Within Run CV | Total CV |
|---|---|---|---|---|---|
| 3.0 | 80 | .13969 | 3.0 | 0.37% | 0.51% |
| 16.5 | 78 | .72842 | 16.45 | 1.24% | 1.30% |
| 20.9 | 80 | .79173 | 20.86 | 0.65% | 1.47% |
| 38.4 | 79 | .97579 | 37.86 | 0.65% | 0.88% |
| 48.5 | 77 | 1.02077 | 48.31 | 0.73% | 1.06% |

The element gives accurate and precise results.

The invention has been described in detail with particular reference to preferred embodiments thereof, but it will be understood that variations and modifications can be effected within the spirit and scope of the invention.

We claim:

1. A multilayer analytical element comprising a support coated in the following order, top down to the support:
    a) a spreading layer,
    b) a dye layer comprising tyrosinase and a hydrazone coupling agent,
    c) a reagent layer comprising salicylate hydroxylase and nicotinamide adenine dinucleotide (NADH), characterized in that
    d) the dye layer has a pH greater than 6.5;
    e) the dye layer and reagent layer are separated by a barrier layer that prevents passage of molecules having a molecular weight in excess of 5,000, and
    f) the hydrazone coupling agent is water insoluble at a pH above 6.5.

2. The element of claim 1, wherein the barrier layer is a hardened gelatin.

3. The element of claims 1 or 2, wherein the dye layer, the barrier layer and the reagent layer each comprise hardened gelatin.

4. The elements of claims 1 or 2, wherein the spreading layer comprises barium sulfate.

5. The element of claims 1 or 2, wherein the spreading layer comprises titanium dioxide.

6. The element of claims 1 or 2, wherein the hydrazone coupling agent is 3-methyl-2-benzothiazolinone hydrazone hydrochlorine (MBTH).

7. The element of claim 6, wherein the pH of the barrier layer and the reagent layer is about 8.0.

8. A dry analytical element for assaying salicylate comprising a support having the following layers, top down to the support:
    a) a spreading layer;
    b) a reagent layer comprising salicylate hydroxylase, (NADH), tyrosinase and a hydrazone coupling agent, characterized in that
    c) the hydrazone and the salicylate hydroxylase are in separate zones of the reagent layer separated by barrier zone that prevents passage of molecules having a molecular weight greater than 5,000;
    d) the zone in which the hydrazone coupling agent is located has a pH greater than 6.5 and;
    e) the hydrazone is water soluble at a pH above 6.5.

* * * * *